(12) United States Patent
Lorant et al.

(10) Patent No.: US 6,616,917 B2
(45) Date of Patent: Sep. 9, 2003

(54) TRANSPARENT OR TRANSLUCENT EMULSIONS, PROCESS FOR PREPARING THEM AND COSMETIC USE THEREOF

(75) Inventors: Raluca Lorant, Thiais (FR); Isabelle Bara, Paris (FR); Martin Josso, Paris (FR); Sandrine Vernaire, Sevres (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/138,243

(22) Filed: May 6, 2002

(65) Prior Publication Data

US 2002/0172703 A1 Nov. 21, 2002

Related U.S. Application Data

(63) Continuation of application No. 09/693,995, filed on Oct. 23, 2000, now Pat. No. 6,419,909.

(30) Foreign Application Priority Data

Nov. 5, 1999 (FR) .............................. 99 13912

(51) Int. Cl.[7] .............................. A61K 7/42; A61K 7/06
(52) U.S. Cl. ...................... 424/59; 424/70.1; 424/70.9; 424/400; 424/401; 514/844; 514/957
(58) Field of Search ................ 424/401, 70.9, 424/400, 59, 70.1; 514/844, 957

(56) References Cited

U.S. PATENT DOCUMENTS

| 4,690,774 | A |   | 9/1987  | Vishnupad et al. |         |
|-----------|---|---|---------|------------------|---------|
| 5,216,033 | A |   | 6/1993  | Pereira et al.   |         |
| 5,456,906 | A |   | 10/1995 | Powell et al.    |         |
| 5,612,043 | A | * | 3/1997  | Deprez et al.    | 424/401 |
| 5,753,240 | A | * | 5/1998  | Bollens et al.   | 424/401 |
| 5,833,997 | A | * | 11/1998 | Mahieu et al.    | 424/401 |
| 5,851,539 | A | * | 12/1998 | Mellul et al.    | 424/401 |
| 6,002,038 | A | * | 12/1999 | Philippe et al.  | 556/420 |
| 6,224,851 | B1 | * | 5/2001 | Bara             | 424/59  |

FOREIGN PATENT DOCUMENTS

| EP | 0 609 131 A1    |   | 8/1994  |
|----|-----------------|---|---------|
| EP | 0 639 371 A1    |   | 2/1995  |
| EP | 1064989         |   | 3/2001  |
| FR | 2 773 064       |   | 7/1999  |
| WO | WO-94/09754 A1  | * | 5/1994  |
| WO | WO 99/63951     |   | 12/1999 |

* cited by examiner

*Primary Examiner*—Jose' G. Dees
*Assistant Examiner*—Marina Lamm
(74) *Attorney, Agent, or Firm*—Nixon & Vanderhye, P.C.

(57) ABSTRACT

The invention relates to a transparent or translucent cosmetic emulsion comprising an aqueous phase, a fatty phase and a surfactant, the said fatty phase containing a miscible mixture of at least one cosmetic oil and of at least one volatile fluoro compound, the latter compound being present in a proportion such that the refractive index of the fatty phase is equal to ±0.05 of that of the aqueous phase.

The invention also relates to the process for preparing the emulsion.

Use of the emulsion in skincare, hair conditioning and antisun protection and/or artificial tanning.

75 Claims, No Drawings

TRANSPARENT OR TRANSLUCENT EMULSIONS, PROCESS FOR PREPARING THEM AND COSMETIC USE THEREOF

This application is a continuation of application Ser. No. 09/693,995, filed Oct. 23, 2000, now U.S. Pat. No. 6,419,909, the entire content of which is hereby incorporated by reference herein.

The present invention relates to transparent or translucent emulsions which are preferably of the oil-in-water (O/W) or water-in-oil (W/O) type based on at least one volatile fluoro compound, to a process for their preparation and to their use in cosmetics.

The present invention relates most particularly to cosmetic emulsions intended in particular for skincare, hair conditioning, antisun protection and/or artificial tanning.

As is known, emulsions consist essentially of two immiscible phases, one being fatty and the other aqueous, and of a surfactant whose role is to stabilize the dispersion of one of the phases, which is present in the form of dispersed droplets, in the continuous phase. Depending on the proportion of the two phases in the emulsion, it is said to be of the oil-in-water type when the aqueous phase is the continuous phase, or of the water-in-oil type when the fatty phase is the continuous phase.

Emulsions are commonly used in cosmetics since they offer great flexibility in formulations and in cosmetic applications. Specifically, they can include a wide variety of active ingredients of very different nature and can be in various forms such as creams or gels that vary in fluidity or thickness.

However, these emulsions generally have a whitish appearance and consequently users find them relatively unappealing. This appearance results essentially from phenomena of deviation by refraction and reflection of the light rays at the interface of the two phases. This opacity is particularly observed in the case of antisun products, since certain sunscreens have high refractive indices, which accentuates the deviation phenomena.

Various processes have been envisaged in order to minimize the deviation of light rays and thus increase the transparency of the compositions.

Among these processes, mention may be made of processes which consist in reducing the diameter of the droplets of the dispersed phase of the emulsion, either by phase inversion, which is found, however, to be difficult, or by adding high proportions of surfactants and treatment in a high-pressure machine. However, in the latter case, the microemulsions thus obtained have the drawback of causing certain skin discomfort and irritation reactions, thus making them cosmetically unacceptable, due essentially to the excess surfactant.

A process has also been proposed which consists in increasing the refractive index of the aqueous phase by adding glycol or glycerol, so as to bring its refractive index closer to that of the fatty phase. However, this process requires the addition of an often large proportion of glycol or glycerol and the emulsions thus obtained have genuinely unpleasant aspects such as a sticky cosmetic feel, as well as problems of discomfort when they are applied.

Moreover, the addition of glycol or glycerol may not be sufficient to obtain compositions with good transparency, due to the generally high refractive index of certain sunscreens.

It is moreover known practice to prepare transparent antisun or self-tanning compositions in the form of aqueous or aqueous-alcoholic gels; however, liposoluble sunscreens cannot be used in aqueous gels and these gels are only very sparingly water-resistant.

As for the aqueous-alcoholic gels, they have the drawback of containing high proportions of alcohol, in particular ethanol, which raises technical problems during their formulation.

It has now been found, surprisingly and unexpectedly, that it is possible to obtain excellent transparent or translucent emulsions by reducing the refractive index of the fatty phase in order for it to be substantially equal to that of the aqueous phase, this being achieved by using a miscible volatile fluoro compound with a refractive index of less than or equal to 1.3.

A subject of the present invention is thus a transparent or translucent emulsion comprising an aqueous phase, a fatty phase and a surfactant, characterized in that the fatty phase contains a miscible mixture of at least one cosmetic oil and of at least one volatile fluoro compound, the latter compound being present in a proportion such that the refractive index of the fatty phase is equal to ±0.05 of that of the aqueous phase, preferably equal to ±0.03 and more preferably equal to ±0.01.

According to the invention, the expression "transparent or translucent emulsion" means an emulsion whose matrix allows light to pass through without causing any deviation by refraction or reflection, or causing only small deviations of the light rays at the interface of the two phases. If the transparency of an emulsion can be readily evaluated with the naked eye, it is generally measured using a turbidimeter. The portable turbidimeter model 2100P® from the company Hach can be used, for example, to measure the ranges of transparency of the emulsions according to the present invention. These emulsions are said to be transparent when the value measured is between 0 and 250 NTU, while they are said to be translucent for a value ranging from 250 to 1000 NTU.

According to the invention, the term "miscible" should be understood as meaning that the mixture is in homogeneous form, i.e. no dephasing takes place between the constituents after they have been placed in contact.

According to the invention, the expression "cosmetic oil" should be understood as meaning any cosmetically acceptable fatty substance that is liquid at 25° C.

The volatile fluoro compound in the fatty phase, used as a mixture with at least one cosmetic oil, is preferably selected from the following compounds:

1) perfluorocycloalkyls corresponding to formula (I) below:

(I)

in which:

n is 2, 3, 4 or 5 m is 1 or 2, and p is 1, 2 or 3 with the proviso that when n=2, m is 2 and when n=3, 4 or 5 and m=2, the fluoro groups are not necessarily alpha to each other;

2) perfluoroalkanes corresponding to formula (II) below:

(II)

in which:
   m is an integer between 2 and 8, and
   X represents Br or F;
3) fluoroalkyls or heterofluoroalkyls corresponding to formula (III) below:

$$CH_3-(CH_2)_n-[Z]_t-X-CF_3 \quad (III)$$

in which:
   X is a linear or branched perfluoroalkyl radical containing from 2 to 5 carbon atoms, and
   Z is O, S or NR, R being a hydrogen or a —$(CH_2)_n$—$CH_3$ or —$(CF_2)_m$—$CF_3$ radical, m being 2, 3, 4 or 5, n is 0, 1, 2 or 3 and t is 0 or 1, and
4) perfluoromorpholine derivatives corresponding to formula (IV) below:

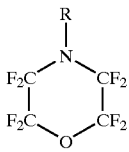

in which R is a $C_1$–$C_4$ perfluoroalkyl radical.

Among the perfluorocycloalkyls of formula (I) which may be mentioned in particular are perfluoromethylcyclopentane and perfluoro-1,3-dimethylcyclohexane, which are sold under the names "Flutec PC1®" and "Flutec PC3®" by the company BNFL Fluorochemicals Ltd. and perfluoro-1,2-dimethylcyclobutane.

Among the perfluoroalkanes of formula (II) which may be mentioned, inter alia, are dodecafluoropentane and tetradecafluorohexane, sold under the trade names "PF5050®" and "PF5060®" by the company 3M or alternatively bromoperfluorooctyl sold under the trade name "Foralkyl®" by the company Atochem.

Among the fluoro compounds of formula (III) which may be mentioned, for example, is nonafluoromethoxybutane and nonafluoroethoxybutane sold respectively under the trade names "HFE-7100®" and "HFE-7200®" by the company 3M.

Finally, among the perfluoromorpholine derivatives of formula (IV) which may be mentioned, for example, is 4-trifluoromethylperfluoromorpholine sold under the trade name "PF5052®" by the company 3M.

These volatile fluoro compounds which have just been defined above all have a refractive index ($n_D^{20}$) of less than 1.43, preferably less than 1.40 and most particularly less than 1.36; they preferably have a saturating vapour pressure, at 25° C., at least equal to 50 Pa; furthermore, they have a boiling point generally of between 25° C. and 65° C. and a high density generally of greater than 1, preferably of greater than 1.2.

The volatile fluoro compound is present in the fatty phase such that the refractive index of the said phase is preferably less than 1.36, its proportion naturally varying as a function of its intrinsic refractive index and of that of the cosmetic oil or mixture of oils. However, its proportion is generally at least 5% and preferably between about 8% and 95% by weight relative to the total weight of the said phase, the remainder consisting of the cosmetic oil or mixture of oils.

According to the invention it is preferred to use volatile fluoro compounds whose solubility parameters are such that they allow homogeneous multiple combinations with other cosmetic oils especially of higher refractive index.

Thus, it is preferably possible to select volatile fluoro compounds whose solubility parameters, according to the Hansen space, correspond to the following criteria:

$\delta d \geq 13$; $\delta p \geq 7$ and $\delta h \geq 3$, measured at a concentration of greater than 10% in a solvent mixture.

The cosmetic oil miscible with the volatile fluoro compound is in liquid form at 25° C. and can be selected from volatile and non-volatile oils, in particular hydrocarbon-based oils of animal origin such as perhydrosqualene, hydrocarbon-based plant oils such as liquid triglycerides of $C_4$–$C_{10}$ fatty acids, linear or branched hydrocarbons of mineral or synthetic origin, synthetic esters or ethers, $C_{12}$–$C_{26}$ fatty alcohols, fluoro oils that are optionally partially hydrocarbon-based and/or silicone-based, the said fluoro oils having a different structure and properties from those of the volatile fluoro compound.

Among the cosmetic oils that are particularly preferred, mention may be made of polysiloxanes, in particular PDMSs and volatile silicone oils, especially cyclic or linear volatile silicones such as cyclotetrasiloxane, cyclopentasiloxane and cyclohexasiloxane and volatile hydrocarbon-based oils such as $C_{11}$–$C_{13}$ isoparaffins and especially isododecane, as well as mixtures of the said oils.

The emulsions according to the invention can be of the oil-in-water or water-in-oil type.

When the emulsions are of the oil-in-water type, the proportion of the aqueous phase is generally between 5% and 95%, preferably between 50% and 95%, and that of the fatty phase is between 0.2% and 94%, preferably between 0.5% and 50%, the surfactant being present in a proportion of from 0.1% to 10% by weight.

On the other hand, when the emulsions are of the water-in-oil type, the proportion of the fatty phase is generally between 10% and 90% and the proportion of the water phase is generally between 10% and 90%, the surfactant being present in a proportion of from 0.1% to 10% by weight.

The surfactant in these emulsions is generally selected from those of the hydrocarbon-based, silicone and/or fluoro type.

When it is desired to obtain an emulsion of the oil-in-water type, an anionic or amphoteric surfactant comprising at least one phosphate or sulphate group is preferably used, such as the surfactants described in patent application FR-2 745 715, the content of which is incorporated into the present description by reference. Among the surfactants of this type which may be mentioned are those sold under the trade names "Pecosil PS-100®", "Pecosil PS-200®" and "Pecosil WDS-100®" by the company Phoenix Chemical. Among the other surfactants which can lead to O/W emulsions, mention may also be made of fluoro surfactants and in particular polyfluorohexylbetaine sold under the trade name "Forafac 1157®" by the company Atochem.

On the other hand, when it is desired to obtain an emulsion of the water-in-oil type, a silicone surfactant is preferably used, in particular those belonging to the family of alkyl- or alkoxy-dimethicone copolyols or alternatively dimethicone copolyols such as those described in patent application FR-2 701 845. Among these surfactants, mention may be made of those sold under the trade names "Abil WE09®", "Abil WS08®", "Abil EM90®" or "Abil EM97®" by the company Goldschmidt, "Q2-5200®", "DC-3225C®" or "DC-5225C®" by the company Dow Corning and "218-1138®", "SF1228®" or "SF1328®" by the company General Electric.

The emulsions according to the invention are particularly useful in cosmetics on account of their pleasant appearance and their multisensory texture combining freshness and softness.

The emulsions according to the invention can be in the form of skincare products, antisun and/or self-tanning products or hair-conditioning products.

Specifically, it has been found that the use of volatile fluoro compounds not only makes it possible to obtain emulsions that have good transparency, but also gives cosmetic properties of feeling pleasant and comfortable as well as an immediate freshness effect from the moment they are applied.

Moreover, the use of at least one volatile fluoro compound makes it possible to obtain a non-sticky, non-greasy film that is particularly light and cosmetic, which may be suitable for use in hot and humid countries.

When the emulsions are intended for skincare, they can contain one or more cosmetic active agents that are soluble in one of the phases, such as, for example, moisturizers, wetting agents, emollients, regenerating agents, weight-reducing agents, decongestants, anti-inflammatories, lightening agents, detoxifying agents, cicatrizing agents or softeners.

When the emulsions are in the form of antisun and/or self-tanning products, a wide variety of lipophilic or hydrophilic sunscreens may be incorporated therein, in particular screening agents with a high refractive index, without the appearance of the emulsion being affected thereby. Furthermore, these emulsions show very good resistance to water and perspiration, and do not leave any residual greasy sensation.

According to this specific embodiment, the emulsions contain one or more organic sunscreens, among which mention may be made of: cinnamic derivatives; dibenzoylmethane derivatives; salicylic derivatives; camphor derivatives; triazine derivatives such as those described in U.S. Pat. No. 4,367,390, EP 863 145, EP 517 104, EP 570 838, EP 796 851, EP 775 698, EP 878 469 and EP 933 376, benzophenone derivatives, β,β'-diphenylacrylate derivatives; benzimidazole derivatives; bis-benzazolyl derivatives such as those described in EP-A-669 323 and U.S. Pat. No. 2,463,264; bis-hydroxyphenylbenzotriazole derivatives such as those described in U.S. Pat. No. 5,237,071, U.S. Pat. No. 5,166,355, GB-A-2 303 549, DE 197 26 184 and EP-A-893 119; p-aminobenzoic acid derivatives; hydrocarbon-based screening polymers and screening silicones such as those described in particular in WO 93/04665.

As examples of sunscreens that are active in the UV-A and/or UV-B range, mention may be made of:

p-aminobenzoic acid,
oxyethylenated (25 mol) p-aminobenzoate,
2-ethylhexyl p-dimethylaminobenzoate,
N-oxypropylenated ethyl p-aminobenzoate,
glyceryl p-aminobenzoate,
homomenthyl salicylate,
2-ethylhexyl salicylate,
triethanolamine salicylate,
4-isopropylbenzyl salicylate,
4-tert-butyl-4'-methoxydibenzoylmethane,
4-isopropyldibenzoylmethane,
2-ethylhexyl 4-methoxycinnamate,
methyl diisopropylcinnamate,
isoamyl 4-methoxycinnamate,
diethanolamine 4-methoxycinnamate,
menthyl anthranilate,
2-ethylhexyl 3,3-diphenyl-2-cyanoacrylate,
ethyl 3,3-diphenyl-2-cyanoacrylate,
2-phenyl-5-benzimidazolesulphonic acid and salts thereof,
3-(4'-trimethylammonium)benzylidene-2-bornanone methyl sulphate,
2-hydroxy-4-methoxybenzophenone,
2-hydroxy-4-methoxybenzophenone 5-sulphonate,
2,4-dihydroxybenzophenone,
2,2',4,4'-tetrahydroxybenzophenone,
2,2'-dihydroxy-4,4'-dimethoxybenzophenone,
2-hydroxy-4-(n-octyloxy)benzophenone,
2-hydroxy-4-methoxy-4'-methylbenzophenone,
α-(2-oxo-3-bornylidene)tolyl-4-sulphonic acid and soluble salts thereof,
3-(4'-sulfo)benzylidene-2-bornanone and soluble salts thereof,
3-(4'-methylbenzylidene)-d,l-camphor,
3-benzylidene-d,l-camphor,
benzene-1,4-bis(3-methylidene-10-camphorsulphonic acid) and soluble salts thereof,
urocanic acid,
2,4,6-tris[p-(2'-ethylhexyl-1'-oxycarbonyl)anilino]-1,3,5-triazine,
2-[p-(tert-butylamido)anilino]-4,6-bis[(p-(2'-ethylhexyl-1'-oxycarbonyl)anilino]-1,3,5-triazine,
2,4-bis{[2-ethyl-4-hexyloxy)]-2-hydroxyphenyl}-6-(4-methoxyphenyl)-1,3,5-triazine,
N-(2 and 4)-[(2-oxo-3-bornylidene)methyl]benzyl] acrylamide polymer,
1,4-bis-benzimidazolylphenylene-3,3',5,5'-tetrasulphonic acid and soluble salts thereof,
2,2'-methylenebis[6-(2H-benzotriazol-2-yl)-4-(1,1,3,3-tetramethylbutyl)phenol],
(2,2'-methylenebis[6-(2H-benzotriazol-2-yl)-4-(methyl) phenol],
polyorganosiloxanes containing a benzalmalonate function,
polyorganosiloxanes containing a benzotriazole function such as "Drometrizole Trisiloxane®".

Among these various sun screen agents, the lipophilic sunscreens preferably used according to the invention are 2-ethylhexyl p-methoxycinnamate sold under the trade name "Parsol MCX®" by the company Givaudan-Rouré, 2-ethylhexyl 3,3-diphenyl-2-cyanoacrylate sold under the trade name "Uvinul N539®" by the company BASF or 4-tert-butyl-4'-methoxydibenzoylmethane sold under the trade name "Parsol 1789®" by the company Givaudan-Rouré, and the hydrophilic sunscreens preferably used according to the invention are terephthalylidenedicamphorsulphonic acid sold under the trade name "Mexoryl SX®" by the company Chimex or 2-phenylbenzimidazole-5-sulphonic acid sold under the trade name "Eusolex 232®" by the company Rona/Merck.

The emulsions can also contain one or more self-tanning agents such as, for example, dihydroxy-acetone (DHA).

The care or antisun and/or self-tanning emulsions according to the invention can also contain any other conventional cosmetic additive.

Among these, mention may be made, for example, of preserving agents, antioxidants, film-forming polymers, soluble dyes and vitamins. Since the subject matter of the invention is the production of transparent or translucent emulsions, it goes without saying that they are virtually free of all insoluble products and in particular of pigment, filler or powder.

Depending on the consistency which it is desired to obtain, the emulsions can optionally contain at least one thickener in a proportion of about from 0.05% to 10%, but preferably between 0.1% and 5% by weight.

The thickener can be selected in particular from:
polysaccharide biopolymers such as xanthan gum, carob gum, guar gum, alginates and modified celluloses such as hydroxyethylcellulose, methylcellulose, hydroxypropylcellulose and carboxymethylcellulose;
synthetic polymers, for instance polyacrylic acids such as the polyglyceryl (meth)acrylate polymers sold under the names "Hispagel®" or "Lubragel®" by the company Hispano Quimica or the company Guardian, polyvinylpyrrolidone, polyvinyl alcohol, crosslinked polymers of acrylamide and of ammonium acrylate sold under the trade names "PAS 5161®" or "Bozepol®" by the company Hoechst, crosslinked polymers of acrylamide and of methacryloyloxyethyl-trimethylammonium chloride sold under the trade name "Salcare SC 92®" by the company Allied Colloids, and magnesium aluminium silicate.

The crosslinked polymers of acrylamide and of 2-acrylamido-2-methylpropanesulphonic acid, also known as AMPS polymers, partially or totally neutralized and sold under the trade name "Sepigel 305®" by the company SEPPIC, are preferably used as thickener. These products are described in particular in patent application EP 503 835, the content of which is incorporated into the present description by reference.

A subject of the present invention is also the process for preparing the transparent or translucent cosmetic emulsions as defined above.

This process consists in adjusting the refractive index of the fatty phase, containing at least one cosmetic oil, with the aid of at least one volatile fluoro compound as defined above, the latter compound being present in the said fatty phase in a concentration such that the refractive index of this fatty phase is equal to ±0.05 of that of the aqueous phase of the emulsion.

More specifically, the process for preparing the transparent or translucent emulsions according to the invention comprises the steps consisting in:

(a) preparing the fatty phase based on at least one cosmetic oil miscible with the volatile fluoro compound,
(b) separately preparing the aqueous phase,
(c) adding at least one surfactant to one of the said phases,
(d) measuring the refractive index of the said fatty and aqueous phases using a refractometer,
(e) adjusting the refractive index of the fatty phase such that it is equal to ±0.05 of that of the aqueous phase, by adding volatile fluoro compound,
(f) emulsifying, with vigorous stirring and in the desired order, the said aqueous phase (b) and the said modified fatty phase (e), at room temperature or with cooling, and
(g) optionally introducing any conventional cosmetic ingredient during the formation of the emulsion.

Several examples of transparent or translucent emulsions in the form of skincare, antisun and/or self-tanning products or hair-conditioning products will now be given by way of illustration.

EXAMPLES

Example 1

Transparent Care Cream

This cream in the form of an O/W emulsion was obtained after preparing the following aqueous and fatty phases:

A—Preparation of the Aqueous Phase:

The aqueous phase was obtained by mixing together the following ingredients:

| | |
|---|---|
| Dimethicone copolyol phosphate ("Pecosil PS100 ®") | 2.40% |
| Sodium hydroxide | 0.06% |

-continued

| | |
|---|---|
| Preserving agents | 0.20% |
| Water | 75.30% |

Refractive index of the aqueous phase $n_D^{20}$=1.345.

B—Preparation of the Fatty Phase:

The fatty phase was obtained from cyclohexasiloxane with a refractive index of 1.405. This value was lowered by addition of nonafluoromethoxybutane to give the following mixture:

| | |
|---|---|
| Cyclohexasiloxane | 8.91% |
| Nonafluoromethoxybutane ("HFE-7100 ®") | 10.88% |

The refractive index of the fatty phase, after mixing, was: $n_D^{20}$=1.345, i.e. identical to that of the aqueous phase.

Formation of the emulsion was then carried out, with vigorous stirring and at room temperature, by introducing the fatty phase into the aqueous phase and simultaneously adding the following ingredients:

| | |
|---|---|
| Xanthan gum | 0.2% |
| AMPS polymer ("Sepigel 305 ®") | 2.0% |

After continuing the stirring for a few minutes, an emulsion having very good transparency and excellent cosmetic properties was obtained.

Example 2

Transparent O/W Emulsion

A transparent O/W emulsion was prepared according to the same procedure as that described in Example 1, using the following aqueous and fatty phases:

| A | Aqueous phase: | |
|---|---|---|
| | Polyfluorohexylbetaine ("Forafac 1157 ®"). | 7% |
| | Preserving agents | 0.2% |
| | Water | 68.8% |

Refractive index of the aqueous phase $n_D^{20}$ = 1.334.

| B | Fatty phase: | |
|---|---|---|
| | Nonafluoromethoxybutane ("HFE-7100 ®") | 12% |
| | Liquid paraffin | 12% |

Refractive index of the fatty phase $n_D^{20}$ = 1.368.

After homogenization of the two phases with vigorous stirring, an O/W emulsion of excellent transparency was obtained.

Example 3

Transparent Antisun W/O Emulsion

A transparent antisun W/O emulsion was prepared using the following aqueous and fatty phases:

| A | Aqueous phase: | |
|---|---|---|
| | Glycol | 5% |
| | Propylene glycol | 31.9% |
| | Dipropylene glycol | 5% |
| | Water-soluble UV screening agent ("Eusolex 232 ®") | 3% |
| | Sodium hydroxide | 0.4% |
| | NaCl | 2% |
| | Water | 20.7% |

Refractive index of the aqueous phase $n_D^{20}$ = 1.428.

| B | Fatty phase: | |
|---|---|---|
| | Nonafluoromethoxybutane ("HFE-7100 ®") | 6% |
| | Isododecane | 6% |
| | Silicone oil (α,ω-dihydroxylated PDMS/PDMS mixture) | 3% |
| | Dimethicone copolyol ("DC-3225C ®") | 10% |
| | Liposoluble UV screening agent (Parsol MCX ®") | 7% |

Refractive index of the fatty phase $n_D^{20}$ = 1.421.

Formation of the emulsion was then carried out, with vigorous stirring and at room temperature, by introducing the aqueous phase into the fatty phase.

After homogenization of the two phases, an antisun W/o emulsion of very good transparency is obtained.

Example 4

Translucent W/O Emulsion

A translucent W/O emulsion was prepared by introducing, with vigorous stirring, 67.8 g of water into a homogeneous fatty phase consisting of:

| Cyclomethicone (cyclopentasiloxane) | 15 g |
|---|---|
| Nonafluoroethoxybutane ("HFE-7200 ®") | 15 g |
| Cetyldimethicone copolyol ("Abil EM90 ®") | 2.2 g |

Refractive index of the fatty phase: $n_D^{20}$ = 1.351.

After homogenization of the two phases, an emulsion of good translucency is obtained.

What is claimed is:

1. Transparent or translucent cosmetic water-in-oil emulsion comprising an aqueous phase, a fatty phase and a surfactant, wherein the fatty phase contains a miscible mixture of at least one cosmetic oil and of at least one volatile fluoro compound, the latter compound being present and used in a proportion such that the refractive index of the fatty phase is equal to ±0.05 of that of the aqueous phase; said fluoro compound having a saturating vapour pressure, at 25° C., of at least 50 Pa, and a boiling point of between 25° C. and 65° C.

2. Emulsion according to claim 1, wherein the volatile fluoro compound is a perfluorocycloalkyl compound corresponding to formula (I) below:

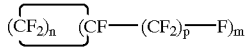

(I)

in which:
n is 2, 3, 4 or 5
m is 1 or 2, and
p is 1, 2 or 3
with the proviso that when n=2, m is 2 and when n=3, 4 or 5 and m=2, the fluoro groups are not necessarily alpha to each other.

3. Emulsion according to claim 1, wherein the volatile fluoro compound is a perfluoroalkane of formula (II) below:

$$CF_3-(CF_2)_m-CF_2X \qquad (ii)$$

in which:
m is an integer between 2 and 8, and
X represents Br or F.

4. Emulsion according to claim 1, wherein the volatile fluoro compound is a fluoroalkyl or a heterofluoroalkyl corresponding to formula (III) below:

$$CH_3-(CH_2)_n-[Z]_t-X-CF_3 \qquad (III)$$

in which:
X is a linear or branched perfluoroalkyl radical containing from 2 to 5 carbon atoms, and
Z is O, S or NR, R being a hydrogen or a $-(CH_2)_n-CH_3$ or $-(CF_2)_m-CF_3$ radical, m being 2, 3, 4 or 5, n is 0, 1, 2 or 3 and t is 0 or 1.

5. Emulsion according to claim 1, wherein the volatile fluoro compound is a perfluoromorpholine derivative corresponding to formula (IV) below:

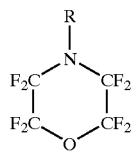

(IV)

in which R is a $C_1-C_4$ perfluoroalkyl radical.

6. Emulsion according to claim 1, wherein the volatile fluoro compound is selected from the group consisting of perfluoromethylcyclopentane, perfluoro1,3-dimethylcyclohexane, perfluoro-1,2-dimethylcyclobutane, dodecafluoropentane, tetradecafluorohexane, bromoperfluorooctyl, nonafluoromethoxybutane, nonafluoroethoxybutane and 4-trifluoromethylperfluoromorpholine.

7. Emulsion according to claim 1, wherein the volatile fluoro compound is present in the said fatty phase in a proportion of at least 5% by weight relative to the total weight of the said phase.

8. Emulsion according to claim 1, wherein the said miscible cosmetic oil is selected from the group consisting of cyclotetrasiloxane, cyclopentasiloxane, cyclohexasiloxane, and isododecane, and mixtures thereof.

9. Emulsion according to claim 1, wherein said emulsion also contains at least one cosmetic active principle.

10. Emulsion according to claim 1, wherein said emulsion also contains at least one sunscreen and/or self-tanning agent.

11. Emulsion according to claim 1, wherein said emulsion also contains at least one conventional cosmetic ingredient.

12. Emulsion according to claim 1, wherein said emulsion also contains a thickener.

13. Emulsion according to claim 1, wherein said emulsion is in the form of a skincare product, an antisun product and/or a self-tanning product or a hair-conditioning product.

14. A process for preparing a transparent or translucent cosmetic emulsion according to claim 1, comprising the step of adjusting the refractive index of the said fatty phase containing at least one cosmetic oil with the aid of the said volatile fluoro compound, said fluoro compound being present in a proportion such that the refractive index of the said fatty phase is equal to ±0.05 of that of the said aqueous phase.

15. The process according to claim 14, comprising of the following steps:
   (a) preparing the fatty phase based on at least one cosmetic oil miscible with the volatile fluoro compound,
   (b) separately preparing the aqueous phase,
   (c) adding the said surfactant to one of the said phases,
   (d) measuring the refractive index of the said fatty and aqueous phases,
   (e) adjusting the refractive index of the said fatty phase such that it is equal to ±0.05 of that of the aqueous phase, by adding the said volatile fluoro compound,
   (f) emulsifying, with vigorous stirring and in the desired order, the said aqueous phase (b) and the said modified fatty phase (e), at room temperature or with cooling, and
   (g) optionally introducing at least one conventional cosmetic ingredient during the formation of the emulsion.

16. Emulsion of claim 4 wherein t=0 and m=3, 4 or 5.

17. Emulsion according to claim 1 wherein the volatile fluoro compound has a refractive index ($n_D^{20}$) of less than 1.43.

18. Emulsion according to claim 2 wherein the volatile fluoro compound has a refractive index ($n_D^{20}$) of less than 1.43.

19. Emulsion according to claim 3 wherein the volatile fluoro compound has a refractive index ($n_D^{20}$) of less than 1.43.

20. Emulsion according to claim 4 wherein the volatile fluoro compound has a refractive index ($n_D^{20}$) of less than 1.43.

21. Emulsion according to claim 5 wherein the volatile fluoro compound has a refractive index ($n_D^{20}$) of less than 1.43.

22. Emulsion according to claim 1 wherein the volatile fluoro compound has a refractive index ($n_D^{20}$) of less than 1.40.

23. Emulsion according to claim 2 wherein the volatile fluoro compound has a refractive index ($n_D^{20}$) of less than 1.40.

24. Emulsion according to claim 3 wherein the volatile fluoro compound has a refractive index ($n_D^{20}$) of less than 1.40.

25. Emulsion according to claim 4 wherein the volatile fluoro compound has a refractive index ($n_D^{20}$) of less than 1.40.

26. Emulsion according to claim 5 wherein the volatile fluoro compound has a refractive index ($n_D^{20}$) of less than 1.40.

27. Emulsion according to claim 1 wherein the volatile fluoro compound has a refractive index ($n_D^{20}$) of less than 1.36.

28. Emulsion according to claim 2 wherein the volatile fluoro compound has a refractive index ($n_D^{20}$) of less than 1.36.

29. Emulsion according to claim 3 wherein the volatile fluoro compound has a refractive index ($n_D^{20}$) of less than 1.36.

30. Emulsion according to claim 4 wherein the volatile fluoro compound has a refractive index ($n_D^{20}$) of less than 1.36.

31. Emulsion according to claim 5 wherein the volatile fluoro compound has a refractive index ($n_D^{20}$) of less than 1.36.

32. Emulsion according to claim 1 wherein the volatile fluoro compound has a density greater than 1.

33. Emulsion according to claim 2 wherein the volatile fluoro compound has a density greater than 1.

34. Emulsion according to claim 3 wherein the volatile fluoro compound has a density greater than 1.

35. Emulsion according to claim 4 wherein the volatile fluoro compound has a density greater than 1.

36. Emulsion according to claim 5 wherein the volatile fluoro compound has a density greater than 1.

37. Emulsion according to claim 1 wherein the volatile fluoro compound has a density greater than 1.2.

38. Emulsion according to claim 2 wherein the volatile fluoro compound has a density greater than 1.2.

39. Emulsion according to claim 3 wherein the volatile fluoro compound has a density greater than 1.2.

40. Emulsion according to claim 4 wherein the volatile fluoro compound has a density greater than 1.2.

41. Emulsion according to claim 5 wherein the volatile fluoro compound has a density greater than 1.2.

42. Emulsion according to claim 13 wherein the volatile fluoro compound has a refractive index ($n_D^{20}$) of less than 1.43.

43. Emulsion according to claim 13 wherein the volatile fluoro compound has a refractive index ($n_D^{20}$) of less than 1.40.

44. Emulsion according to claim 13 wherein the volatile fluoro compound has a refractive index ($n_D^{20}$) of less than 1.36.

45. Emulsion according to claim 13 wherein the volatile fluoro compound has a density greater than 1.

46. Emulsion according to claim 13 wherein the volatile fluoro compound has a density greater than 1.2.

47. Emulsion according to claim 2, wherein said emulsion also contains at least one cosmetic active principle.

48. Emulsion according to claim 3, wherein said emulsion also contains at least one cosmetic active principle.

49. Emulsion according to claim 5, wherein said emulsion also contains at least one cosmetic active principle.

50. Emulsion according to claim 2, wherein said emulsion also contains at least one sunscreen and/or self-tanning agent.

51. Emulsion according to claim 3, wherein said emulsion also contains at least one sunscreen and/or self-tanning agent.

52. Emulsion according to claim 5, wherein said emulsion also contains at least one sunscreen and/or self-tanning agent.

53. Emulsion according to claim 2, wherein said emulsion also contains at least one conventional cosmetic ingredient.

54. Emulsion according to claim 3, wherein said emulsion also contains at least one conventional cosmetic ingredient.

55. Emulsion according to claim 5, wherein said emulsion also contains at least one conventional cosmetic ingredient.

56. Emulsion according to claim 2, wherein said emulsion also contains a thickener.

57. Emulsion according to claim 3, wherein said emulsion also contains a thickener.

58. Emulsion according to claim 5, wherein said emulsion also contains a thickener.

59. Emulsion according to claim 2, wherein said emulsion is in the form of a skincare product, an antisun product and/or a self-tanning product or a hair-conditioning product.

60. Emulsion according to claim 3, wherein said emulsion is in the form of a skincare product, an antisun product and/or a self-tanning product or a hair-conditioning product.

61. Emulsion according to claim 5, wherein said emulsion is in the form of a skincare product, an antisun product and/or a self-tanning product or a hair-conditioning product.

62. A process for preparing a transparent or translucent cosmetic emulsion according to claim 2, comprising the step of adjusting the refractive index of the said fatty phase containing at least one cosmetic oil with the aid of the said volatile fluoro compound, said fluoro compound being present in a proportion such that the refractive index of the said fatty phase is equal to ±0.05 of that of the said aqueous phase.

63. A process for preparing a transparent or translucent cosmetic emulsion according to claim 3, comprising the step of adjusting the refractive index of the said fatty phase containing at least one cosmetic oil with the aid of the said volatile fluoro compound, said fluoro compound being present in a proportion such that the refractive index of the said fatty phase is equal to ±0.05 of that of the said aqueous phase.

64. A process for preparing a transparent or translucent cosmetic emulsion according to claim 5, comprising the step of adjusting the refractive index of the said fatty phase containing at least one cosmetic oil with the aid of the said volatile fluoro compound, said fluoro compound being present in a proportion such that the refractive index of the said fatty phase is equal to ±0.05 of that of the said aqueous phase.

65. Emulsion according to claim 16 wherein the volatile fluoro compound has a refractive index ($n_D^{20}$) of less than 1.43.

66. Emulsion according to claim 16 wherein the volatile fluoro compound has a refractive index ($n_D^{20}$) of less than 1.40.

67. Emulsion according to claim 16 wherein the volatile fluoro compound has a refractive index ($n_D^{20}$) of less than 1.36.

68. Emulsion according to claim 16 wherein the volatile fluoro compound has a density greater than 1.

69. Emulsion according to claim 16 wherein the volatile fluoro compound has a density greater than 1.2.

70. Emulsion according to claim 16, wherein said emulsion also contains at least one cosmetic active principle.

71. Emulsion according to claim 16, wherein said emulsion also contains at least one sunscreen and/or self-tanning agent.

72. Emulsion according to claim 16, wherein said emulsion also contains at least one conventional cosmetic ingredient.

73. Emulsion according to claim 16, wherein said emulsion also contains a thickener.

74. Emulsion according to claim 16, wherein said emulsion is in the form of a skincare product, an antisun product and/or a self-tanning product or a hair conditioning product.

75. A process for preparing a transparent or translucent cosmetic emulsion according to claim 16, comprising the step of adjusting the refractive index of the said fatty phase containing at least one cosmetic oil with the aid of the said volatile fluoro compound, said fluoro compound being present in a proportion such that the refractive index of the said fatty phase is equal to ±0.05 of that of the said aqueous phase.

* * * * *